United States Patent [19]

Siemer

[11] Patent Number: 4,888,985
[45] Date of Patent: Dec. 26, 1989

[54] METHOD AND APPARATUS FOR TESTING TAPE BOND STRENGTH

[76] Inventor: Dennis K. Siemer, 217 Viking Dr., Mankato, Minn. 56001

[21] Appl. No.: 332,599

[22] Filed: Apr. 3, 1989

[51] Int. Cl.$^4$ .............................................. G01N 19/04
[52] U.S. Cl. ................... 73/150 A; 73/842; 73/827; 73/829
[58] Field of Search ................ 73/150 R, 150 A, 827, 73/829, 834, 842

[56] References Cited

U.S. PATENT DOCUMENTS

| | | | |
|---|---|---|---|
| 2,473,517 | 6/1949 | Freedman | 73/150 A |
| 2,724,264 | 11/1955 | Dart et al. | 73/828 |
| 2,834,205 | 5/1958 | Pickup | 73/827 |
| 2,912,855 | 11/1959 | MacAllister et al. | 73/792 |
| 2,982,129 | 5/1961 | Wetzel et al. | 73/827 |
| 2,989,865 | 6/1961 | Belfour | 73/827 |
| 3,019,644 | 2/1962 | Mancini | 73/150 A |
| 3,183,711 | 5/1965 | Duncan | 73/828 |
| 3,394,588 | 7/1968 | Mohle et al. | 73/150 A |
| 3,396,578 | 8/1968 | Skundberg | 73/827 |
| 3,412,606 | 11/1968 | Cooper et al. | 73/150 A |
| 3,524,345 | 8/1970 | Isaacson | 73/150 A |
| 3,537,301 | 11/1970 | Hasenwinkle | 73/834 |
| 3,580,065 | 5/1971 | Strittmater | 73/150 A |
| 3,674,221 | 7/1972 | Riemersma | 73/828 |
| 3,678,740 | 7/1972 | Schmid et al. | 73/827 |
| 4,194,392 | 3/1980 | Lombard et al. | 73/827 |
| 4,302,979 | 12/1981 | Dykmans | 73/828 |
| 4,548,083 | 10/1985 | Schuerer et al. | 73/827 |
| 4,628,742 | 12/1986 | Golding | 73/829 |
| 4,637,252 | 1/1987 | Rhee et al. | 73/827 |

FOREIGN PATENT DOCUMENTS

| | | | |
|---|---|---|---|
| 1948897 | 4/1971 | Fed. Rep. of Germany | 73/150 A |
| 56-27636 | 3/1981 | Japan | 73/150 A |
| 57-44834 | 3/1982 | Japan | 73/150 A |
| 1536864 | 12/1978 | United Kingdom | 73/827 |

Primary Examiner—William A. Cuchlinski, Jr.
Assistant Examiner—Diego F. F. Gutierrez
Attorney, Agent, or Firm—Harold D. Jastram

[57] ABSTRACT

The method and apparatus employs a frequency sensitive electric motor and control system to measure the adhesive bond between a carrier tape and a cover tape adapted to carry miniature components. The adhesive bond strength is dynamically tested and recorded by separating the cover tape from the carrier tape as an energizing signal of predetermined frequency is applied to a frequency sensitive motor for a predetermined period of time while the force required to cause adhesive bond failure is measured and recorded.

23 Claims, 10 Drawing Sheets

METHOD AND APPARATUS FOR TESTING TAPE BOND STRENGTH

FIELD OF THE INVENTION

The invention relates to a method and apparatus for testing or measuring the force required to separate a cover tape from a carrier tape used to carry small components during the course of manufacturing of products utilizing miniature parts such as computer chips. The device dynamically measures the bond strength of employed on storage tapes.

Miniaturization of a wide variety of electrical and mechanical components has lead to a wide variety of modern day products which are becoming increasingly more compact. Success has been realized in miniaturizing many modern-day products including calculators, computers, watches and similar products. Development of smaller and more powerful microchips used in the operation of such products has led to increasingly more compact products.

As products have become increasingly miniaturized, there has occurred an increase in the problems with handling the miniature components during the course of manufacturing.

Competitive demands also have required that the cost of manufacturing such miniaturized products be increasingly automated in order to reduce labor costs, handling costs and storage costs. These assembly, storage and handling demands have lead to employment of techniques and products which can be used in these increasingly automated assembly processes in order to insure delivery of the miniature components to the automated assembly line without damage and without loss of the component. In a typical such process, microchips which are to be incorporated into a device such as a calculator or computer, are stored in reels containing a prescribed number of such components. These reels of components are formed by providing a storage tape which has discrete pockets at prescribed distances along a carrier tape into which microcomponents are placed. A cover tape is placed over the carrier tape to individually capture and isolate the component in a secure container. These storage tapes are then rolled on reels containing a prescribed number of such components. The components stored in this fashion can then be easily transported from manufacturer to user, stored in warehouses where necessary and ultimately used on the production line for delivering the microchip or miniature component to the assembly line for incorporation in finished compact products.

It will be apparent then that the reels of storage tapes containing individually packaged components act as a method of inventorying the components since each reel will contain a prescribed number of such components. Further, the reels are much more easily packaged, shipped and handled than the individual microchips which they contain. Accordingly, the microchips can be stored in the protected environment of the pocket of the carrier tape where if need be, the pockets with the cover tape form a controlled atmosphere and physical protection for the microchip or similar miniature device.

This reel delivery system, however, creates its own potential problems and needs. In the typical highly automated manufacturing assembly line, robotics are increasingly employed and controlled by computers in order to automate the assembly process. Reels of microcomponents are brought to the assembly line where the cover tape is stripped away from the carrier tape by robotic mechanisms under the control of computer software programs. The robotic assembly systems, however, are designed and adjusted to perform mechanical functions by applying force to various components and materials in order to carry out the assembly process. These assembly procedures carried out by the robotic equipment employ application of forces normally within a prescribed force range. For example, the cover tape of a typical reel of storage tape must be removed in order to gain access to the component carried by a carrier tape. The forces necessary to remove the cover tape from the carrier tape may vary widely with the result that work stoppage, breakage and similar problems may be encountered. This assembly interruption occurs if the robotic equipment has not been set to apply force to the tape removing process which falls within the acceptable range necessary to accomplish the removal of the cover tape to gain access to the miniature component.

Consequently, a prerequisite to efficient and uninterrupted assembly of miniature components requires that the robotic assembly equipment be adjusted within a known range of force necessary to remove cover tape from a carrier tape. The force necessary to remove a cover tape from a carrier tape therefore must be known so that proper adjustment may be made to the robotic assembly equipment and proper operating limits may be established in the computer controlling the assembly process. If the amount of force necessary to peel the cover tape from the carrier tape is known, the robotic equipment used in the assembly process can be effectively set to accomplish the removal of the cover tape from a carrier tape with efficiency and without error. This will insure that the assembly process will function smoothly and without interruption. It is apparent, however, that an important criteria, that of knowing the precise limits of the peel force necessary to remove the cover tape, is a critical and indispensable parameter which must be known in order to insure the efficient operation of such robotic assembly operations.

SUMMARY OF THE INVENTION

The present invention is directed to an improvement in the design and method of testing the peel forces required to remove a cover tape from a carrier tape in a reel of encapsulated components.

The present invention is characterized by simplicity of design, ease of applying reels of storage tapes to the testing device and the precision with which such tapes of different sizes may be tested in varying ranges of force necessary to remove a cover tape from a carrier tape.

The device and method employed by the invention contemplates testing the removal of a cover tape from a carrier tape at varying rates of speed of removal. The rate of removal of a cover tape from a carrier tape will influence the amount of force required to accomplish that removal. Accordingly, the test apparatus employs a stepper motor which can be varied in the rate of operation in order to test the removal forces at varying dynamic rates. A stepper motor is controlled by a control module employing a generator having variable frequency output. As the output of a frequency from the frequency generator is changed, the stepper motor will operate at different but known rates of speed. With such a control, precise adjustment of operation of the stepper motor can be controlled to measure the force necessary to remove a cover tape. Thus, the testing apparatus can determine the peel force necessary to remove a cover tape from a carrier tape under a dynamic operating condition of a robotic assembly line.

Another object of the invention is to provide a simple mechanism employing a motor which permits ease of mounting a storage tape on the testing device for testing. To this end, the present invention employs a sprocket system which engages apertures on the edge of a storage tape which are similar to the sprocket apertures employed in connection with 35 mm photographic film. A sprocket and idler roller arrangement adaptable to receive tapes of varying widths, is cooperative with a rack and pinion mechanism driven by the stepper motor to permit ease of mounting of a reel of storage tape on the test apparatus. A cover tape is attached to a strain gauge which then senses the amount of force necessary to remove the cover tape from the carrier tape as the stepper motor is activated by a variable frequency generator. The output of the strain gauge is an electrical signal which activates a recorder to record the magnitude and time period of the applied force to remove the cover tape from the carrier tape.

DESCRIPTION OF THE DRAWINGS

For a better understanding of the invention, reference should be made to the accompanying drawings, wherein.

DETAILED DESCRIPTION

Figure 1:
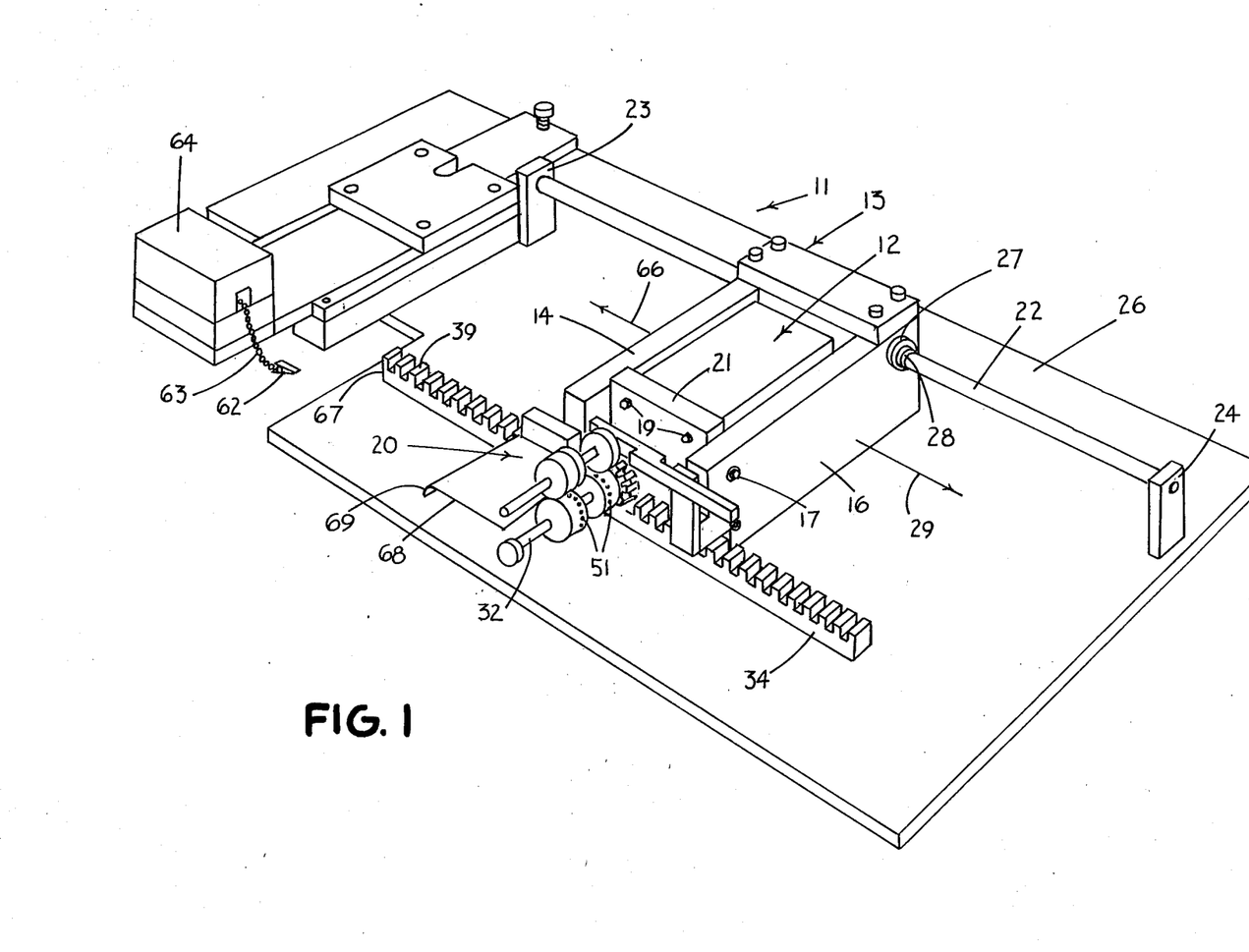
FIG. 1 is an isometric view of an apparatus in accordance with the present invention illustrating a carrier tape engaged by the test apparatus.

A more full understanding of the invention can be realized by reference first to FIG. 1 of the drawings which is an isometric view of the entire tester generally designated by the numeral 11. The major components of the peel tester include an electric motor 12 which is mounted in a housing 13. The motor 12 is mounted between walls 14 and 16. Motor 12 is mounted between these walls 14 and 16 in a standard fashion which would include bolting the motor 12 to the wall 16 by a bolt or screw 17. A similar bolt 18 would appear in wall 14 to bolt the motor 12 to the wall 14. See FIG. 4 of the drawings.

Also, the motor 12 is bolted by bolts 19 to a carrier plate 21 so that the electric motor 12 is securely mounted in the housing 13 for movement with the housing 13.

The walls 14 and 16 of housing 13 extend beyond the motor 12 and engage a guide bar 22. Guide bar 22 is anchored at each end by a bracket 23 and 24. Each of these brackets, 23 and 24, are securely attached to a chassis, or base, 26. The guide bar 22 is a cylindrical bar of material sufficiently stiff to carry the weight of the housing 13 and motor 12.

The housing 13 is mounted on the guide bar 22 by a slide bearing 27. Bearing 27 is a friction bearing which may utilize a variety of materials such as teflon, nylon or brass to slidably engage the cylindrical guide bar 22. A similar slide bearing 27 is also mounted in wall 14 so that the entire housing 13 carrying the motor 12 can move in the arrow directions 29 and 31 as illustrated in FIG. 1 of the drawings. Thus it will be apparent that the housing 13 can move fully along the length of carrier or guide bar 22.

Figure 8:
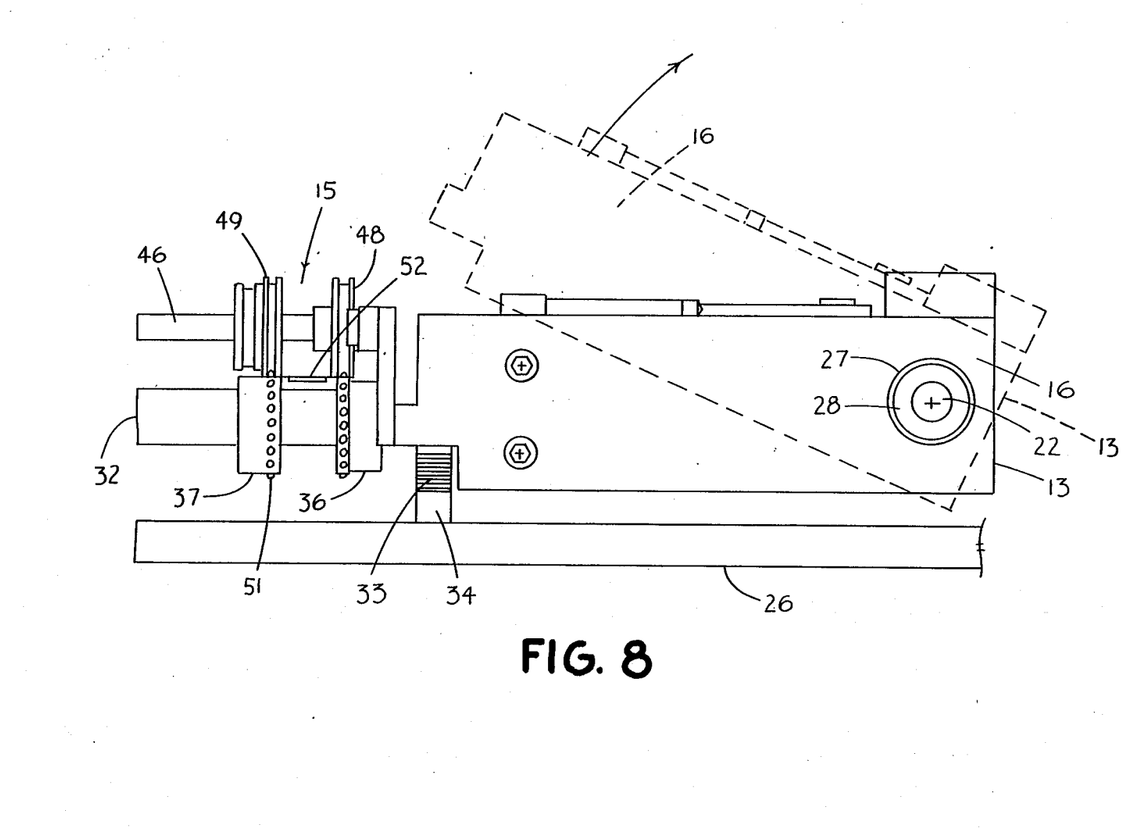
FIG. 8 is a right end view of an apparatus illustrated in FIG. 1 of the drawings.

In addition to serving as a guide for the housing 22, the guide bar 22 also acts as a pivot to permit the housing 13 to be pivoted about guide bar 22. The pivoting feature of the housing and guide bar is illustrated in FIG. 8 of the drawings where the solid lines in the drawing illustrate a first or closed position of the housing 13 and the dotted lines illustrate the pivoted position of the housing 13. It is noted in FIG. 8 that the housing 13 can be pivoted in the clockwise direction about the guide bar 22 to permit the housing 13 carrying the motor 12 to be pivoted above the plane of the chassis or base 26. This pivoting feature is accomplished through the use of slide bearings 27 which not only permit the housing to move longitudinally along the length of the guide bar 22 but also permit the housing 13 to be pivoted about the guide bar 22 on the plastic or metal bearings 28. The feature permits efficient and easy movement of the motor 12 and housing 13 in a longitudinal direction along guide bar 22. This pivotal feature will become more apparent and the use will become readily apparent in connection with a further description of the mechanism.

Figure 4:
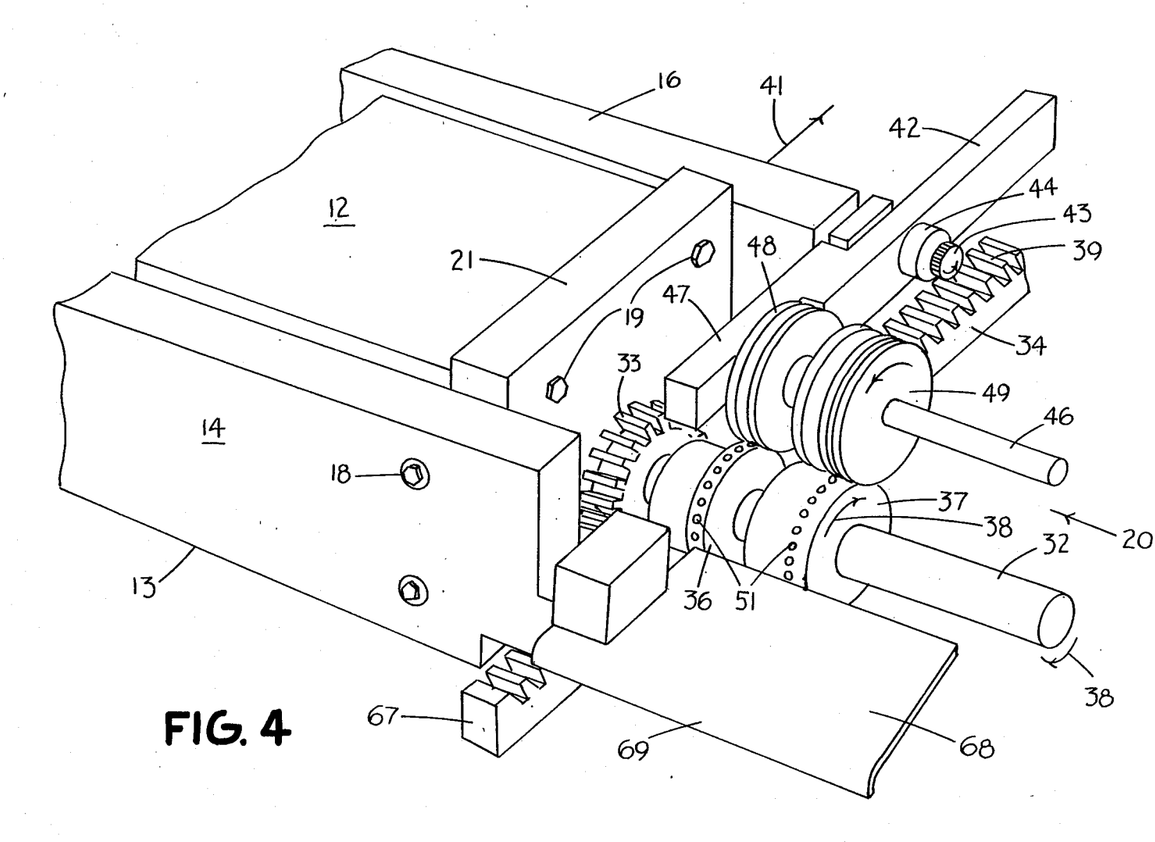
FIG. 4 is a left fractional isometric view illustrating a rack and pinion and sprocket arrangement.

Next refer to FIG. 4 of the drawings. Drive shaft 32 is driven by motor 12. A pinion 33 is mounted on shaft 32 and driven by the motor 12 along a rack 34. Also mounted on shaft 32 are a pair of sprockets 36 and 37. As motor 12 rotates shaft 32 in the clockwise or arrow direction 38, the pinion 33 which engages the teeth 39 of rack 34 will carry the housing 13 and the attached motor 12 to the right or in the arrow direction 41 as illustrated in FIG. 4 of the drawings.

At the same time that pinion 33 is moving the motor 12 and housing 13 along the rack 34, the drive shaft 32 is also rotating the sprockets 36 and 37 in the clockwise direction as illustrated in FIG. 4 of the drawings. The function of these sprockets 36 and 37 is to drive a storage tape 52 having apertures or perforations 58 in the edges of the tape at a predetermined rate as will be hereinafter more fully explained in connection with a description of the other drawings.

An idler arm 42 is mounted on the housing 13. Idler arm 42 may be bolted by a bolt 43 to the wall 16 of housing 13 or it may be attached by other well-known mechanical methods and means. Idler arm 42 may be mounted on wall 16 by a bolt 43 which secures a pivot bearing 44 in contact with the idler arm 42. Thus, the idler arm 42 can be rotated about bolt 43. Bolt 43 can be utilized to immobilize the idler arm 42 in any predetermined position by merely tightening the bolt 43.

An idler shaft 46 is mounted on end 47 of idler arm 42. A pair of idler rollers 48 and 49 are mounted on shaft 42 so that the rollers 48 and 49 rotate in the counter clockwise direction as illustrated in the drawing in FIG. 4, when the sprockets 36 and 37 rotate in the clockwise direction. Idler rollers 48 and 49 engage a top surface of a storage tape 52 which is being driven by sprockets 36 and 37 to insure that the tape 52 constantly engages, or positively engages, the teeth 51 of the sprockets 36 and 37.

Figure 6:
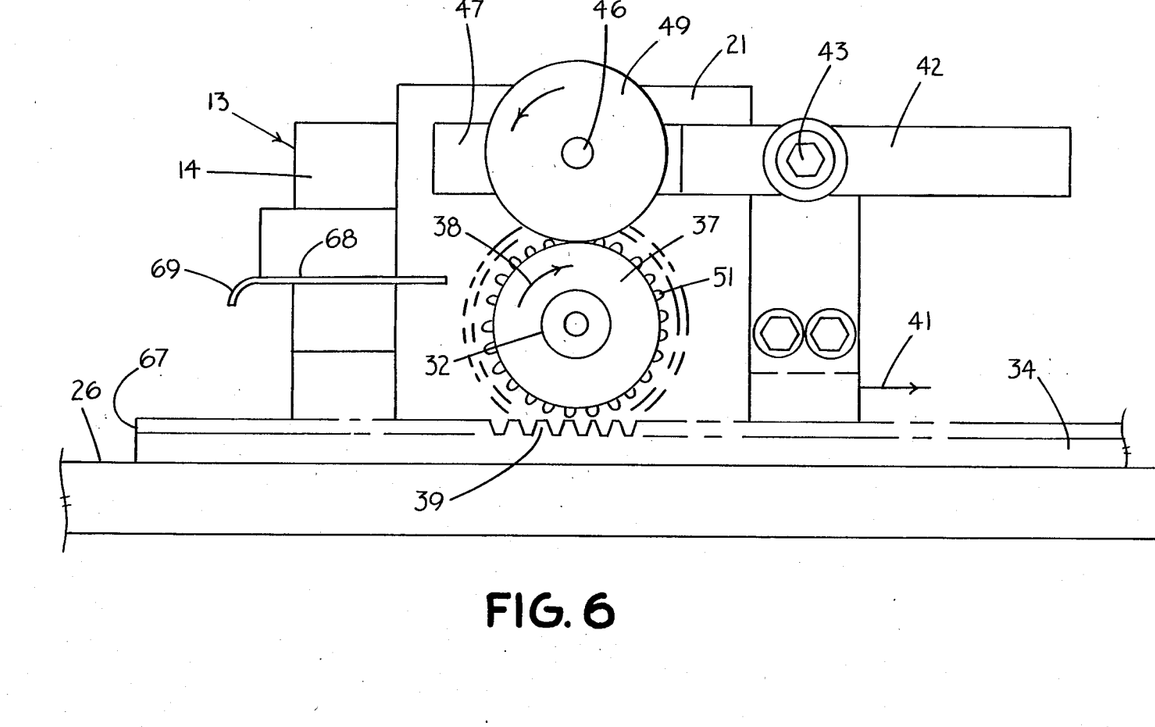
FIG. 6 is a fractional front view of a rack and pinion and sprocket arrangement illustrated in FIG. 1 of the drawings.

The rotational relationship of the components can be more fully understood from reference to FIG. 6 of the drawings where idler arm 42 carrying idler roller 49 is shown in a front view. It will be noted that when the motor 12 is driving sprocket 37 in the clockwise direction, the engaged idler roller 49 which has been pivoted into position in contact with sprocket 37 about pivot bolt 43 will be rotating in the counter clockwise direction. Thus, any tape which is in contact with the sprocket teeth 51 will be positively held into engagement with the sprocket 37 by the idler roller 49 as the sprocket 37 drives the tape in the arrow direction 41 illustrated in FIG. 6 of the drawings. At the same time that the sprocket 37 is being rotated in the clockwise direction as illustrated in FIG. 6 of the drawings, the pinion gear 33 (not shown in FIG. 6) will be driving the pinion along rack 34 in the arrow direction 41.

Figure 9:
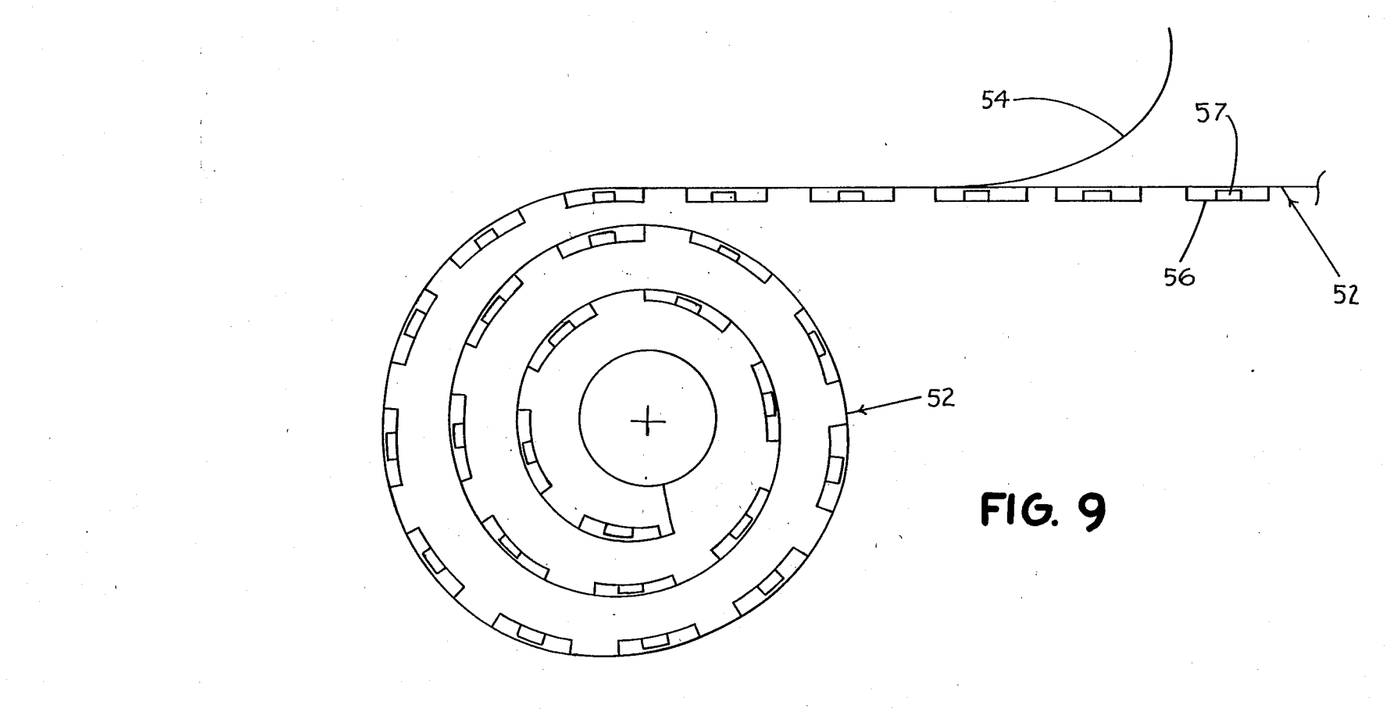
FIG. 9 is a plan view of a carrier tape tested by the apparatus of the invention.

Referring again to FIG. 4 of the drawings, it will become apparent that the pinion 33, drive sprockets 36 and 37, idler rollers 48 and 49, and the rack 34 all cooperate as a unit to provide a drive mechanism generally designated by numeral 20 adapted to engage a storage tape 52 such as that illustrated in FIG. 9 of the drawings, to move the tape 52 to the right as viewed in FIG. 4 of the drawings, along the arrow direction 41 when the motor 12 is activated.

The storage tape 52 typically used in robotic manufacturing processes is illustrated in FIG. 9 of the drawings. Typically, these storage tapes 52 are composed of a carrier tape 53 and a cover tape 54. In the manufacture of electronic equipment and similar products employing small components such as memory chips, transistors, tiny bolts and similar components, difficulty in storing and handling the products is encountered. Further, delivery of such tiny components to the manufacturing assembly location is also a troublesome process. These problems have been solved by utilizing a storage tape 52 of the type depicted in FIG. 9 of the drawings where a carrier tape 53 is composed of a series of pockets 56 in the surface of the carrier tape 53 which are used as receptacles or containers for small components 57. In order to entrap a small component 57 in the pocket 56, a cover tape 54 is placed over top of the carrier tape 53 thereby ensuring that component 57 will remain in the pocket 56 during storage or delivery to the assembly line. Long lengths of these storage tapes 52 are then rolled into reels as illustrated in FIG. 9 for storage, transportation or mounting on robotic delivery equipment at the assembly line. These long rolls of storage tape 52 can be employed with a predetermined number of components 57 per roll of tape. In this way, the tapes also act as an inventory device. Counting of the rolls is all that is necessary to determine the number of components 57 in inventory.

Figure 3:
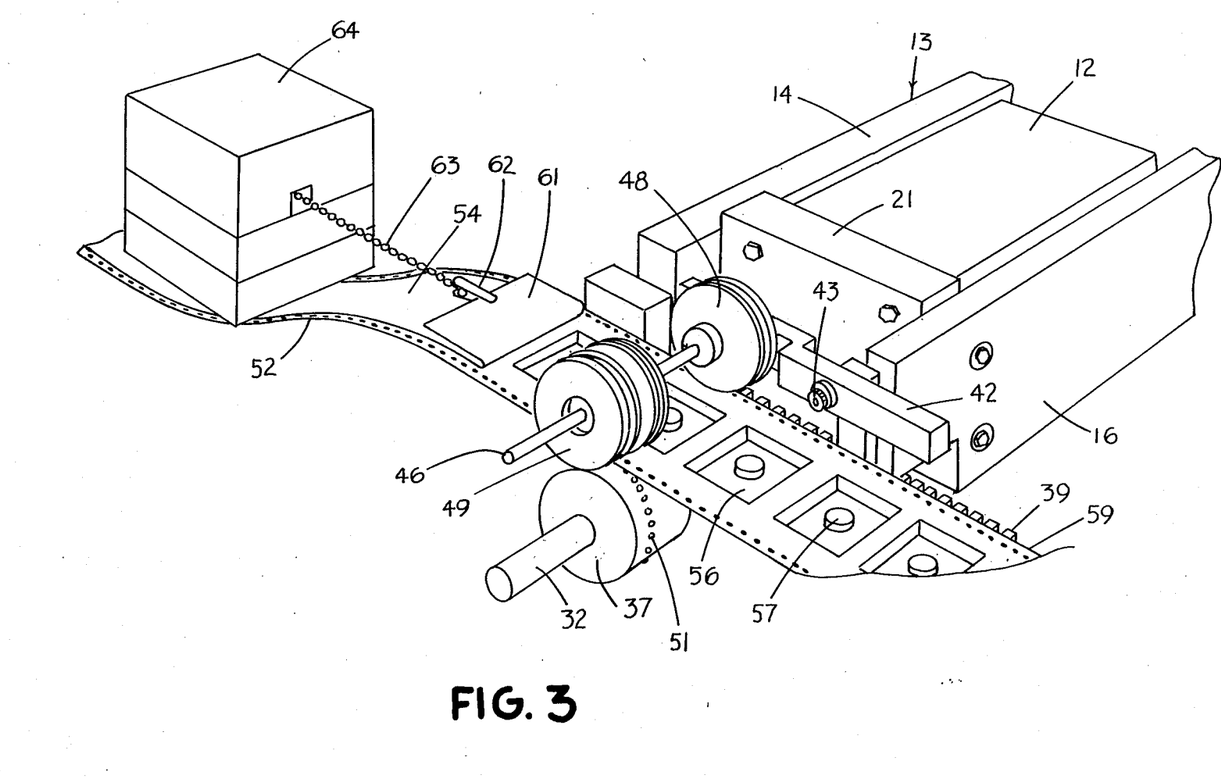
FIG. 3 is a fractional right side isometric view of FIG. 1 illustrating a rack and pinion and sprocket mechanism.
Figure 5:
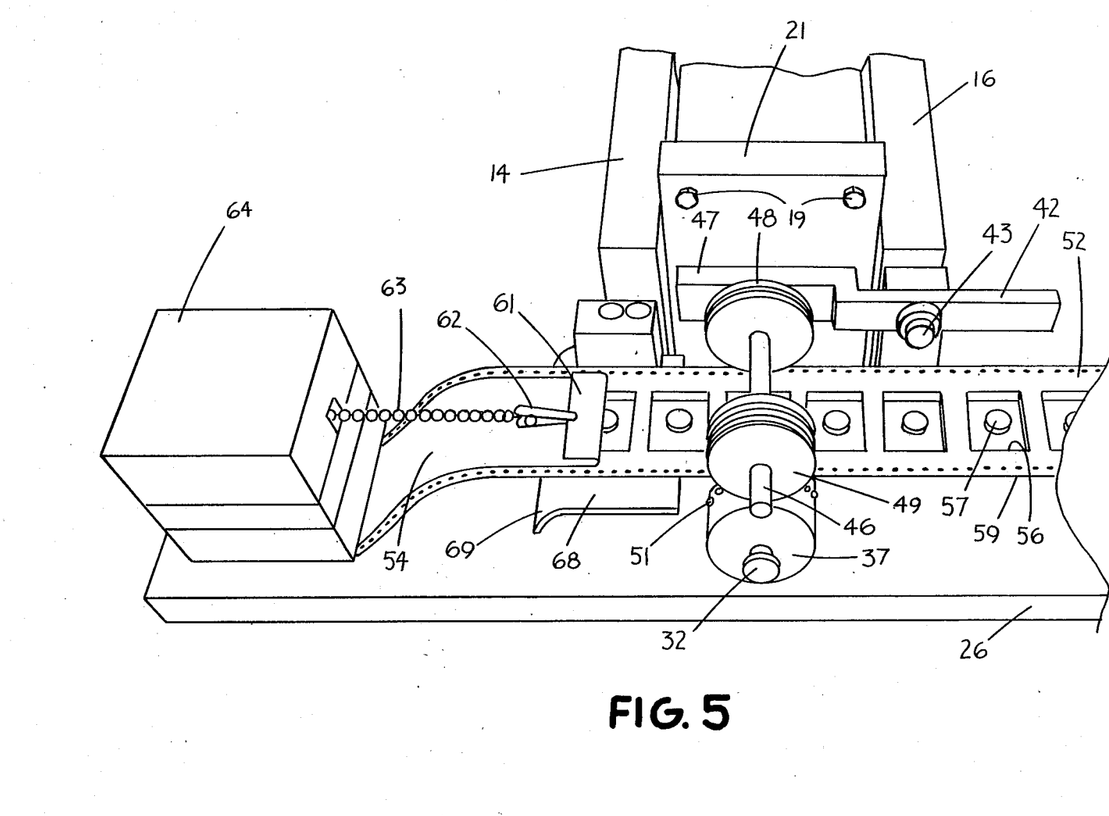
FIG. 5 is a top isometric view illustrating a rack and pinion mechanism in association with a sprocket.
Figure 7:
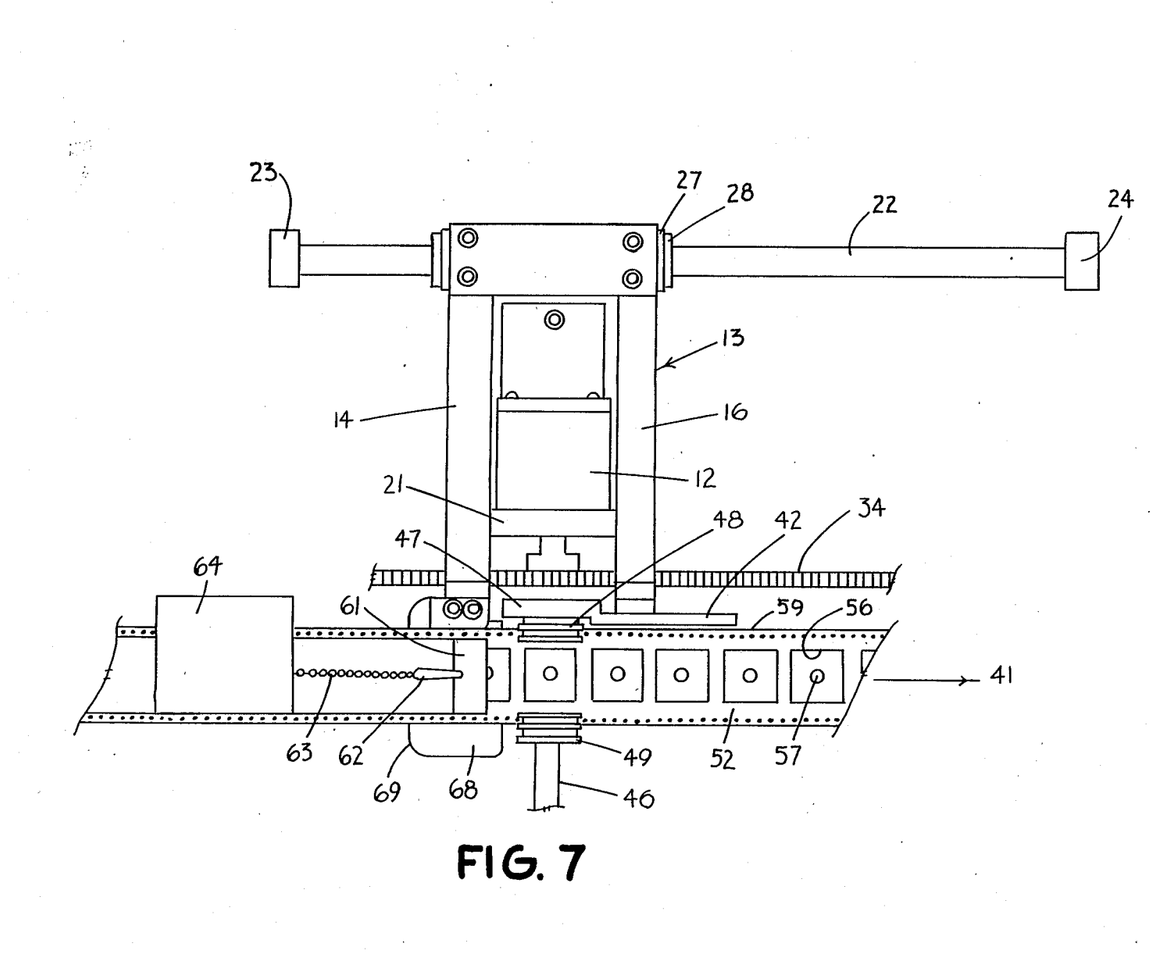
FIG. 7 is a top fractional view of an apparatus illustrated in FIG. 1 of the drawings.

These storage tapes 52 are illustrated in perspective view in FIGS. 3 and 5 of the drawings. The pockets 56 provide convenient cavities for encapsulating and carrying the components 57. In order to move the storage tape 52 along an assembly line for removal of the components 57, the storage tape 52 is provided with a series of perforations 58 on the edges 59 of the storage tape 52. These perforations 58 are engaged by the teeth 51 of the sprockets 36 and 37 in order to positively drive the storage tape 52 in the arrow direction 41. The arrow direction is illustrated in FIGS. 6, 4 and 7 and also by arrow 29 of FIG. 1.

In order to gain access to the components 57 during the manufacturing process, the cover tape 54 must be removed from the carrier tape 53 so that access to the components 57 is convenient and uninterrupted. This requires that the cover tape 54 be stripped away from the carrier tape 53. The force necessary to remove the cover tape 54 from the carrier tape 53 is the focus of the present invention. Computer controlled assembly systems employing a variety of robotic assembling devices require that each aspect of the assembly process be accurately controlled. One feature of the control required for assembly of small components is the requirement that they be delivered to the assembly line at a predetermined and regular interval. This is readily accomplished by employing a storage tape of the type illustrated in FIG. 9 of the drawings. A further problem encountered during the manufacturing process, however, is the problem of gaining access to the component in order that it can be incorporated into a larger product. Since the component 57 must be removed from the carrier tape, this also requires that the cover tape 54 be removed from the carrier tape. Use of computer controlled machinery requires that the force required to remove the cover tape 54 from the carrier tape 53 be known within prescribed parameters.

Knowing the stripping force necessary to remove the cover tape 54 from the carrier tape 53 is of such importance that an Electronics Industry Association (EIA) standard has been established for the force required to remove a cover tape from a carrier tape. This standard force has been established to be 10 to 70 grams of force. While this EIA standard is followed by many manufacturing firms, others have adopted stripping forces which far exceed the maximum force of the standard level. For example, some manufacturers are willing to employ storage tapes which require stripping or peel forces of as much as 130 grams and possibly slightly more. These higher stripping forces are permissible because much of the machinery which is employed in the assembly process can be adjusted to accommodate these higher stripping forces. It is important, however, that the stripping force is a known parameter.

Experience has illustrated that storage tapes 52 are assembled with a wide variety of adhesives cementing the carrier tape 53 and the cover tape 54. Also, experience has illustrated that varying storage conditions will affect the adhesive bond between the cover tape 54 and carrier tape 53. Environmental conditions such as temperature, radiation moisture content of the environment, and similar factors will affect the adhesive bond between the carrier tape 53 and the cover tape 54. Also, many adhesives undergo changes in the bonding strength with aging caused by chemical reaction. Therefore, while the storage tape 52 may be manufactured with a precise and well-known bonding strength between the carrier tape 53 and the cover tape 54, this bond may increase or decrease as the carrier tape 52 is transported from assembly to storage and later to the assembly line where it is employed.

In order to ensure successful and uninterrupted assembly on the assembly line, manufacturers have learned that testing of each of the storage tapes 52 is a prudent process before the storage tape is introduced to the manufacturing line. For this reason, packaging of small components in such storage tapes usually provides for a leader at the beginning of each reel of storage tape 52 so that the manufacturer can peel or strip the cover tape 54 from the carrier tape 53 and actually measure the force required to remove the cover tape 54. It is this test for which the present invention and process is specifically devised. The apparatus is constructed to provide easy application of the storage tape to the sprockets 36 and 37 and a convenient and accurate apparatus and method for testing the force necessary to remove the cover tape 54 from the carrier tape 53.

Figure 2:
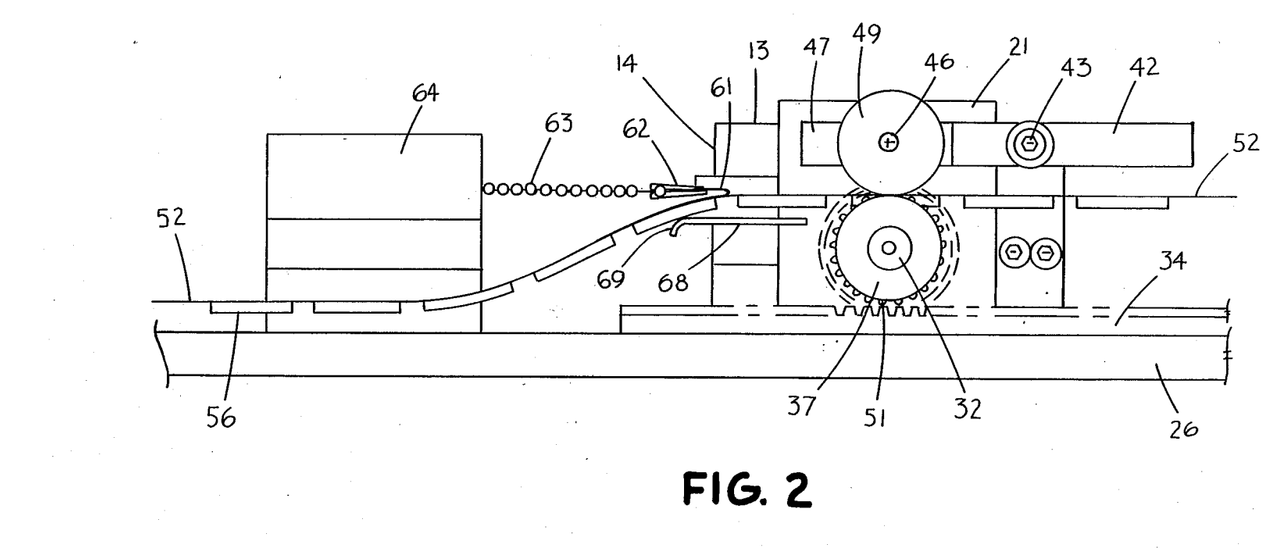
FIG. 2 is a front view of the apparatus illustrated in FIG. 1 of the drawings.

The method and apparatus for undertaking such tests using the present apparatus and method can continue to be illustrated by again referring to FIG. 6 of the drawings. A leader of the storage tape 52 can be applied to the teeth 51 of the sprockets 36 and 37 by pivoting end 47 of the idler arm 42 in the clockwise direction about pivot bolt 43 to rotate the idler rollers 48 and 49 upwardly as viewed in FIG. 6 of the drawings. The storage tape 52 is then laid upon the sprockets 36 and 37 so that the perforation 58 on the edges of the storage tape 52 engage the teeth 51 of each of the sprockets 36 and 37. The storage tape 52 is applied to the sprockets 36 and 37 with the pockets carrying the components 57 in a downwardly position as illustrated in FIG. 2 of the drawings.

Next, the idler arm 42 is rotated in a counter clockwise direction as viewed in FIG. 6 of the drawings so that the idler rollers 48 and 49 engage the storage tape 52 along the edge of the tape in contact with the perforated edge 59. Idler rollers 48 and 49 are separated a sufficient distance so that the idler rollers 48 and 49 individually contact only the perforated edge of the storage tape 52 and do not engage the area of the storage tape 52 occupied by the cover tape 54. Next, a small portion of the lead end 61 of the cover tape 54 is stripped away form the carrier tape 53 and connected to a strain gauge clip 62. Clip 62 is connected through a flexible connector 63 to a standard strain gauge 64.

Another feature of the invention will be apparent from a reference to FIG. 8 of the drawings. Storage tapes 52 frequently are manufactured in varying widths. These widths may vary from 8 to 56 millimeters. Such a wide divergence in the width of the storage tape 52 requires some accommodation in the mechanics of the tester if storage tapes 52 of such widely varying sizes are to be tested on the same mechanism. Accordingly, the entire drive mechanism 20 which includes the sprocket, idler rollers and pinion 33 are specifically designed to accommodate tapes 52 of widely different dimension. Drive shaft 32 and idler shaft 46 are extended beyond idler roller 49 and sprocket 37 so that the idler and sprocket may be adjusted along the length of the shafts 32 and 46 to provide for different sized tapes 52. If a relatively narrow tape 52 is to be tested by the tester, the idler roller 49 and the sprocket 37 may be positioned along shafts 46 and drive 32 respectively as illustrated in FIG. 8 of the drawings. On the other hand, if a much larger carrier tape 52 is to be accommodated, the idler roller 49 and the sprocket 37 may be moved along the shafts 46 and 32 away from idler roller 48 and sprocket 36 to provide greater distance between the sprockets and idler rollers. This permits the present invention to accommodate a wide range of tape sizes and yet perform the testing function without making great adjustments in the drive train, and similar components of the drive mechanism 20.

Since the strain gauge 64 connector 63 is of limited length, and because the force testing operation will require a stripping of the cover tape 54 away from the carrier tape 53, the motor 12, which is preferably a stepper motor, needs to be positioned near the strain gauge 54. The motor 12, including the housing 13 and the drive mechanism composed of the sprockets and idler rollers, can all be moved along the guide bar 22 toward to strain gauge 64. This step can be readily observed by reference to FIG. 1 of the drawings in which the stepper motor 12 is illustrated positioned in the middle of rack 34. The entire assembly can be moved closer to the strain gauge 64 by merely grasping the housing 13 or the shaft 32 and lifting the entire assembly upward as viewed in FIG. 1 of the drawings. By lifting the housing 13 upwardly as illustrated in FIG. 1 or at better illustrated in FIG. 8, the housing 13 will pivot about guide bar 22 on bearings 27. The raised housing 13 can then be moved in the arrow direction 66 toward the strain gauge 64. By rotating the housing 13 upwardly as illustrated in FIG. 8 of the drawings, the pinion 33 driven by motor 12 will disengage the teeth 39 of the rack 34. When the housing 13 is guided or slid longitudinaly along guide bar 22 to the end 67 of the rack 34, it can then be re eased to rotate the housing 13 in the counter clockwise direction as viewed in FIG. 8 of the drawings so that the entire assembly including the housing 13, motor 12 and the drive mechanism 20 is then positioned back on rack 34 with the pinion 33 in contact with the teeth 39. In this position, the carrier tape 52 can then be applied to the sprockets 36 and 37 as previously described in connection with rotation of the idler arm 42 and idler rollers 48 and 49. In this position, also, the carrier tape 54 is stripped back and attached to clip 62.

When these steps have been carried out, the storage tape 52 is now positioned and ready to be tested for the stripping or peel force necessary to remove cover tape 54 as illustrated in FIG. 2 of the drawings. In FIG. 2, it is noted that the storage tape 52 is guided to the sprockets 36 and 37 by a platform 68 which has a slightly curved lead 69 to ensure that the pockets 56 of the storage tape 52 will be easily guided onto the platform 68 and into contact with the teeth 51 of sprockets 36 and 35. FIG. 5 of the drawings also illustrates the positioning of the storage tape 52 when it is in position to be tested. It is noted that the clip 62 securely engages lead end 61 in preparation for testing the force necessary to remove the cover tape 54 from the carrier tape 53.

When the storage tape 52 is thus positioned in the drive mechanism 20 of the assembly, the steppermotor 12 is ready to be energized in order to begin the testing procedure.

When energy is applied to the motor 12, the motor will begin to drive pinion 33 and sprockets 36 and 37 as previously described toward end 65 of rack 34.

After the carrier 13 has been moved to the extreme end 67 of rack 34, and the storage tape has been loaded onto sprockets 36 and 37, the idler rollers 48 and 49 rotate in contact with the storage tape 52. Next, end 61 of the cover tape 54 is peeled back and attached to clip 62. When these steps have been accomplished, the tester is now in a condition for testing the peel force necessary to remove the cover tape 54 from the carrier tape 53.

At this point, the stepper motor 12 is energized and the motor begins to drive pinion 33 along rack 34 to the right or in the arrow direction as indicated by arrow 41 of FIG. 6 or by arrow 29 in FIG. 1.

As stepper motor 12 begins this drive function, the sprockets 36 and 37 rotate on drive shaft 32 to begin to drive the carrier tape 53 through the drive mechanism 20 and apply force to the storage tape 52. Again, it is noted that the carrier tape 53 of the storage tape 52 contains perforations 58 which are engage by the teeth 51 of the sprockets 36 and 37 to drive the carrier tape through the drive mechanism.

As motor 12 is activated, the end 61 of cover tape 54 is immobilized by the clip 62 so that the cover tape 54 is stripped away from the carrier tape 53. When this occurs, force is applied to flexible connector 63 which in turn is connected to strain gauge 64. String gauge 64 is a standard device designed to measure linear forces applied to the connector 63 and to generate an electrical output proportional to the amount of force applied to the flexible connector 63. Consequently, an electrical output from strain gauge 64 is generated which is indicative of the force necessary to strip or peel the cover tape 54 from carrier tape 53.

Figure 10:
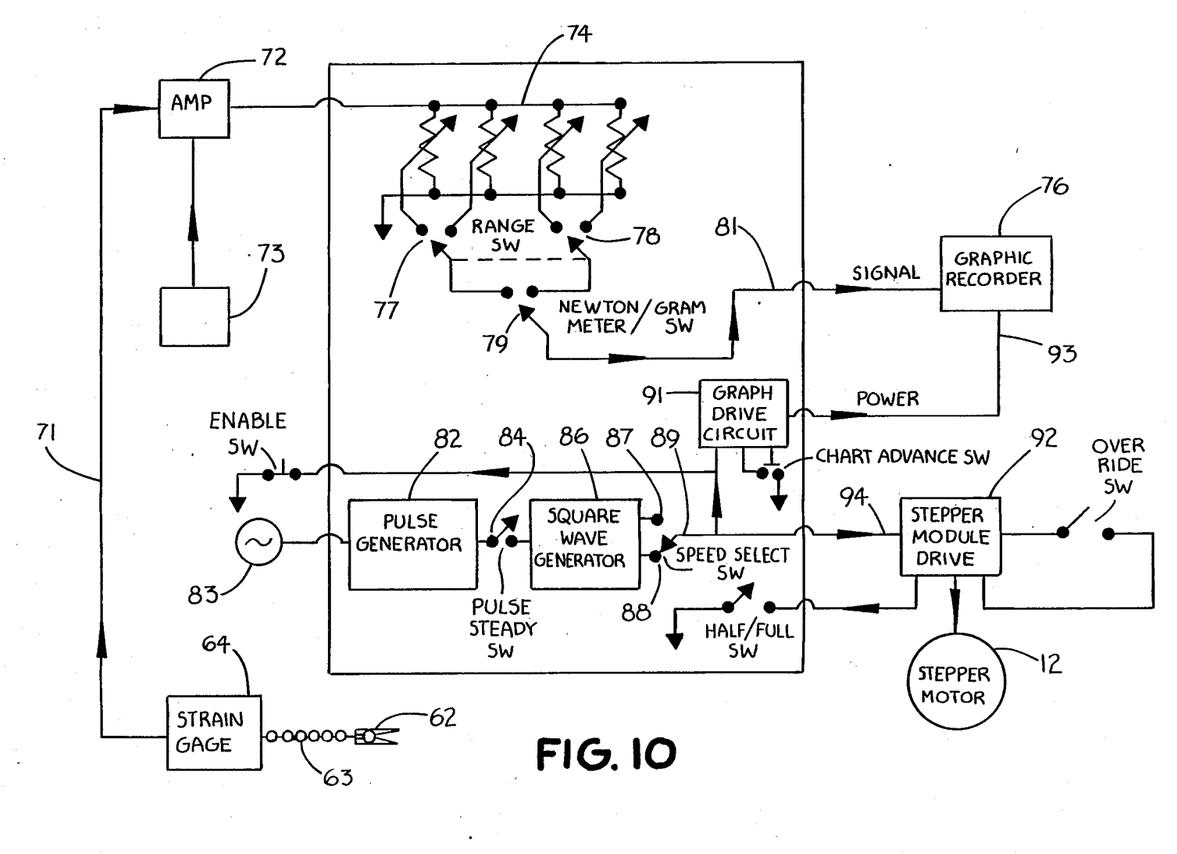
FIG. 10 is a block diagram illustrating the various functions and relationship of mechanical and electrical components employed in the invention.

Refer next to FIG. 10 of the drawings which illustrates an electrical system designed to energize stepper motor 12 and incorporating the output from strain gauge 64 for measuring and recording the force necessary to strip cover tape 54 from carrier 53. A signal output from strain gauge 54 is applied via line 71 to amplifier 72. Amplifier 72 is energized by power supply 73. The combination of the power supply 73 and amplifier 72 is a typical combination designed to amplify the signal generated by strain gauge 64.

The output from amplifier 72 is applied to scale potentiometers 74. Potentiometers 74, which includes the indicated switches and variable resistors, is a standard system designed to vary the range of the signal which is applied to graphic recorder 76. For instance, potentiometers 74 may be utilized to accommodate stripping pressures in two differing ranges. The potentiometers 74 might permit measurement of stripping forces on first scale from zero to 100 grams of force, whereas a second range of force might be accommodated in the zero to 200 gram range. If a lower range of zero to 100 grams is the range in which stripping testing is to occur, the potentiometer switches 77, 78 and 79 might be positioned in the left-most position as viewed in FIG. 10 of the drawings. In this range, a signal would be applied along line 81 to a recorder 76 which falls within the range of zero to 100 grams of force. In the event, however, that stripping force will lie in the 200-gram range, switches 77, 78 and 79 can be moved in tandem to the 200-gram range of the potentiometer 74 so that the output signal on line 81 will be in the 200-gram range. In this fashion, the present invention permits testing of stripping forces which lie in different range of force.

As is apparent, a signal from strain gauge 64 will thus be applied via line 71 to amplifier 72 where an output signal from amplifier 72 indicative of the stripping force necessary to remove cover tapes 54 is applied to potentiometers 74 and ultimately to a graphic recorder 76 or some other type of recorder in order to make a record of the stripping force being applied to the cover tape 54.

The next major portion of the electrical system which operates the tester involves that part of the electrical circuitry which controls the stepper motor 12. In this circuit, a pulse generator 82 is energized by an A/C power source 83. The signal from pulse generator 82 is applied through switch 84 to a square-wave generator 86. Square-wave generator 86 is actually two generators which generate a signal having different frequencies. A first frequency output from terminal 87 can be selectively chosen in preference to a second frequency output from terminal 88 if a different speed for stepper motor 12 is desired. The square-wave generator in effect acts as a signal frequency speed control for the stepper motor 12 since the stepper motor operational speed is directly dependent on the frequency of the power signal applied to drive the motor 12.

If the switch 89 is positioned as indicated in FIG. 12 to select a frequency from terminal 88, this output signal will be applied to a graphic drive circuit 91 and to stepper module drive 92. The signal applied to the graphic drive circuit 91 applies power via line 93 to the graphic recorder 76 in order to begin to record the magnitude and duration of the output signal arriving at the graphic recorder from line 81. A typical example of a graphic recorder might be simply the type that drives a sheet of paper past a recording pin which records the magnitude of the signal. Thus it will be apparent that the same signal which is activating the stepper motor 12 is also activating the graphic recorder 76.

The square-wave signal at a preselected frequency is applied to the steppermodule drive 92 via line 94. The stepper module drive 92 is a standard drive commonly employed to control a stepper motor 12 which is the preferred motor employed with the present invention. The preference for the use of a stepper motor 12 is derived from the fact that speed control can be achieved very easily by simply varying the frequency of the power signal from the square-wave generator 86. If a different speed is required to operate stepper motor 12, then the switch 89 may simply be moved to terminal 87 so that a different frequency is applied to the stepper module drive 92 to change the speed of the operation of stepper motor 12. This ability to change the speed of operation of the steppermotor 12 is important since it eliminates the need for elaborate mechanical devices to change the speed of operation of the pinion 33. In other testing devices, changes to the gears and gear ratios are required. Such changes are time consuming and require costly alternate equipment whereas the stepper motor 12 permits rapid and easy change of speed.

Precise control of the speed of operation of the testing device is important because there are also standards of testing the stripping force of storage tapes 52 which involve carrying out the test for stripping force at a specific linear speed. EIA procedures call for the testing of stripping forces to be carried out within specific ranges of speed at which the cover tape 54 is pulled away from the carrier tape 53. The EIA standard calls for this parameter to be within 120 millimeters per minute of speed. A European standard, as an example, calls for the speed of such a test to be at 300 ml per minute. Consequently, it will be apparent that an important feature of this invention is the ability to vary the speed of the stepper motor 12 to accommodate more than one stripping speed in order to carry out a test of the storage tape 52. As noted, this variation of speed is readily achieved by simply varying the frequency output from the square-wave generator 86 and applying the drive signal at a selected frequency to the stepper module drive 92 which in turn controls the drive signal applied to stepper motor 12. Thus, this invention employs the unique characteristic of a stepper motor 12 in operating at predetermined speeds determined by the frequency of the power signal applied to the motor.

Another feature of the present invention is a stepper module drive 92 which permits operation of the motor 12 for a precise period of time. The module drive 92 is a typical module drive having a standard timing circuit designed to apply power to the stepper motor 12 for a precise period of time. The module drive 92 simply incorporates on and off timing circuits which apply power to the motor 12 for a preselected period of time so that the Motor operated at the preselected frequency signal or speed for a time period as determined by the drive module 92.

This feature permits the test mechanism to test the stripping force necessary to remove cover tape 54 from carrier tape 53 in intermittent steps similar to those which will be experienced when the storage tape is employed in an assembly procedure. In the typical assembly line procedure, the storage tape is driven intermittently so that only a single pocket 56 is exposed at a given time. The typical assembly line process calls for access to a component part 57 on an intermittent basis. Accordingly, the mechanisms used to remove the cover tape 54 from the carrier tape 53 will intermittently energize the system to remove the cover tape 54 from only a single pocket 56. This start and stop operation of the mechanism introduces dynamic forces into the tape-stripping operation which the present mechanism is capable of testing. Since a stepper motor 12 is employed, it can be energized on a selective basis by the module drive 92 for a given period of time sufficient to start the stripping process for a sufficiently long period of time to expose only one pocket 56. This stripping operation is carried out at a preselected speed which is typical of an assembly line speed and then the stepper motor 12 is stopped. These start and stop operations are sensed by the force applied to the connector 63 and the detected by the strain gauge 64. Consequently, the present invention permits the testing of the peel forces characteristic of the storage tape 52 under the same dynamic conditions that tape 52 will experience when it is employed in an assembly line process.

Thus it will be apparent that the present invention provides a method for testing the peel forces necessary to remove a cover tape 54 from a carrier tape 53 which precisely records the pressure or force range experienced by such a procedure. In order to carry out the full testing process, a first step can involve immobilizing the carrier tape 53 by applying it to the teeth 51 of sprockets 36 and 37. The teeth 51 engage perforations 58 and thereby result in a connection of this particular layer of the storage tape to a stepper motor 12 through the drive mechanism. Next, a portion, end portion 61, of the cover tape 54 is immobilized by connecting it to a clip 62. The stepper motor 12 is then energized with an electrical drive signal of predetermined frequency generated by the square-wave generator 86 and is applied to the motor 12 for a predetermined period of time as selected by the module drive 92. The stepper motor 12 applies sufficient force to the storage tape 52 through the sprockets 36 and 37 and drive pinion 33 to separate the cover tape 54 from the carrier tape 53. This separation force which effectively causes the bond between the cover tape 54 and the carrier tape 53 to fail, is measured or detected by the strain gauge 64. The magnitude of the signal generated by the strain gauge 64 is indicative of the magnitude of force which causes the bond between the tapes to fail. This signal output from strain gauge 64 is then directed through a potentiometer 74 to a recorder 76 which records the magnitude of that signal. The recorder also records the time duration that the force is applied and the variation of that force as the stepper motor 12 applies the force since the recorder is designed to record the magnitude of a signal over the time period of a signal applied to the motor.

Thus it will be apparent that the present invention provides an effective method and an apparatus for measuring the separation force necessary to remove a cover tape 54 from a carrier tape in order to give an operator of a robotic processing assembly line an accurate indication of the forces necessary to expose components in a storage tape 52. The invention has the flexibility to measure such forces within differing ranges. The use of a potentiometer capable of detecting signals in different ranges is useful in testing peel forces falling in differing force ranges and indeed for testing tapes which are manufactured for use in differing manufacturing environments. As an example, the present invention can be used to test tapes using parameters set forth by European standards as well as for testing tapes designed to fall within U.S. standards for such tape bonding strength.

The method and apparatus also provides a way of varying the speed of separation testing by utilizing a stepper motor 12 which can easily be varied in speed by merely applying a different frequency drive signal to the motor. This important aspect of the invention eliminates the need for complicated mechanical gearing and changes in such gearing in order to accommodate different testing standards.

The above-described specific mechanisms and process employed in the present invention are merely illustrative of the principles of the invention. A number of variations might be employed to change various features of the invention without departing from the spirit and scope thereof. For instance, the idler arm 42 may be spring biased by applying spring force to the end 47 or the opposite end. Application of a spring force to idler arm 42 would then permit a greater application of force to the edges 59 of the carrier tape 53 in order to ensure positive engagement of the teeth 51 by the perforations 58 when the stepper motor 12 applies driving force through pinion 33. Further, a variety of methods might be used to mount stepper motor 12 in the housing 13.

Also, in the electrical circuitry, a variety of components might be utilized in order to provide pulse generators, square-wave generators, and module drive which carry out the operating principles of the invention. These and other changes may be made to the invention and still fall within the spirit and scope of the invention.

What is claimed is:

1. A device for testing the bond strength between first and second bonded layers of a laminated material which comprise a motor means, chassis means, a guide means mounted on said chassis means, track means mounted on said chassis, drive means powered by said motor means and engaging said track means, said motor means being mounted on said guide means, gauge means for restraining said first bonded layer and for measuring the force applied to said first layer, engaging means mounted on said motor means and driven by said motor means for engaging said second bonded layer, energizing means for selectively applying power to said motor means to activate said drive means to move said drive means and motor means along said track means and said guide means to apply force to said second bonded layer, said engaging means moving laterally away from said gauge means to apply force to the bond between the first and second bonded layers, said gauge means detecting the force applied to said layer and recording means responsive to said gauge means for recording the magnitude of the force measured by said gauge means.

2. A device in accordance with claim 1 in which said motor means is a stepper motor.

3. A device in accordance with claim 1 in which said energizing means includes a variable frequency pulse generator adapted to generate an output drive signal at selected frequencies to vary the speed of operation of said motor means.

4. A device in accordance with claim 1 which further includes a range selection means interconnecting said gauge means and recording means for changing the range of signal sensitivity of said recording means.

5. A device in accordance with claim 1 in which said track means is a rack and in which said drive means includes a pinion driven by said motor means.

6. A device in accordance with claim 1 in which said laminated material has apertures along at least one edge of said laminated material in said second layer and in which said engaging means includes a first sprocket for engaging said apertures.

7. A device in accordance with claim 6 in which said track means is a rack and in which said drive means includes a pinion with said first sprocket mounted on a common drive shaft driven by said motor means.

8. A device in accordance with claim 7 which further includes a second sprocket mounted on said common drive shaft and in which said laminated material has apertures along two edges of said laminated material, said first and second sprockets engaging apertures on said two edges of said laminated material.

9. A device in accordance with claim 8 in which one of said first and second sprockets can be moved along said common drive shaft to accommodate laminated material of different widths.

10. A device in accordance with claim 9 which further includes an idler means mounted on said chassis means, said idler means having an idler roller for contacting said laminated material to force the aperture bearing edges of said laminated material into positive engagement with said first and second sprockets.

11. A device in accordance with claim 10 in which said idler means is pivotally mounted on said chassis means to permit said idler roller to be pivoted out of engagement with said first and second sprockets to permit ease of mounting of said laminated material on said sprockets.

12. A device in accordance with claim 11 in which said drive means and motor means pivot about said guide means to permit said pinion to be disengaged from said rack to move said motor means and drive means along the length of said guide means to a first end of said rack where said second bonded layer is attached to said engaging means.

13. A device for testing the bond strength between first and second bonded layers of a laminated material which comprise a movable motor means, chassis means, a guide means mounted on said chassis means, track means mounted on said chassis, drive means powered by said motor means and engaging said track means, said motor means being mounted on said guide mean and movable along said track means, strain gauge means for generating an electrical signal in response to a force applied to said strain gauge means, said strain gauge means adapted to engage a first layer of said laminated material, engaging means operated by said motor means and in cooperation with said drive means for engaging a second layer of said laminated material, energizing means for selectively applying power to said motor means for a predetermined period of time to drive said motor means at a predetermined rate of speed to move said engaging means and second layer to apply a force to said laminated material to separate said first and second layers and thereby generate an electrical signal output from said strain gauge means indicative of the adhesive bond between said first and second layers and recording means for recording the magnitude of said signal.

14. A device in accordance with claim 13 in which said motor means is a stepper motor and in which said energizing means includes a pulse generator adapted to generate an output drive signal at a preselected frequency to control the speed of operation of said stepper motor.

15. A device in accordance with claim 14 in which said pulse generator is a variable frequency pulse generator adapted to vary the speed of operation of said stepper motor by varying the frequency of said pulse generator.

16. A device in accordance with claim 15 which further includes a square wave generator interconnected between said pulse generator and said stepper motor to generate a square wave output drive signal to control the speed of operation of said stepper motor.

17. A device in accordance with claim 13 in which said recording means is a graphic recorder.

18. A device in accordance with claim 13 which further includes a range selection means interconnecting said strain gauge means and said recording means for changing the range of signal sensitivity of said recording means to the signal from said strain gauge means.

19. A method of measuring the force necessary to separate first and second bonded layers of a laminated material which comprises the steps of
  a. immobilizing said first bonded layer,
  b. connecting said second layer to a stepper motor, said stepper motor being movable along a track means
  c. energizing said motor with an electrical signal of predetermined frequency for a predetermined period of time to apply sufficient force to said second layer to separate said second layer from said first layer,
  d. measuring the force necessary to separate said second layer from said first layer,
  e. generating a signal indicative of the magnitude of the force measured when said second layer is separated from said first layer, and then
  f. recording the magnitude of said signal.

20. A method in accordance with claim 19 in which said stepper motor is energized by an electrical signal of predetermined frequency having a square wave form.

21. A method of measuring the force necessary to separate first and second bonded layers of a laminated material which comprises the steps of
  a. connecting said first layer to a force measuring device, b. connecting said second layer to a stepper motor, said stepper motor being movable along a track means
c. generating a pulsating energizing signal of predetermined frequency,
d. applying said energizing signal to said stepper motor for a predetermined period of time to apply sufficient force to said second layer to separate said second layer from said first layer,
e. measuring the magnitude and duration of the force necessary to separate said second layer from said first layer, f. generating a force signal indicative of the magnitude and duration of the force necessary to separate said second layer from said first layer, and then
g. recording the magnitude and duration of said signal.

22. A method in accordance with claim 21 in which the magnitude and duration of said signal is recorded on a graphic recorder.

23. A method in accordance with claim 21 which further includes the step of applying said force signal to a signal range selecting system prior to recording the magnitude and duration of said signal.

* * * * *